United States Patent [19]

Prestel et al.

[11] Patent Number: 4,999,433
[45] Date of Patent: Mar. 12, 1991

[54] PROCESS FOR THE PREPARATION OF BENZOTRIAZOLE DERIVATIVES

[75] Inventors: Helmut Prestel, Bruchsal; Klaus Müller, Lorsch, both of Fed. Rep. of Germany

[73] Assignee: Ciba-Geigy Corporation, Ardsley, N.Y.

[21] Appl. No.: 412,370

[22] Filed: Sep. 26, 1989

[30] Foreign Application Priority Data

Sep. 28, 1988 [CH] Switzerland ........................ 3594/88

[51] Int. Cl.$^5$ ............................................ C07D 249/20
[52] U.S. Cl. .................................... 548/260; 548/261
[58] Field of Search ............... 548/260, 259, 257, 261

[56] References Cited

U.S. PATENT DOCUMENTS

| | | | |
|---|---|---|---|
| 3,978,074 | 8/1976 | Gancis | 548/259 |
| 4,219,480 | 8/1980 | White et al. | 548/260 |
| 4,230,867 | 10/1980 | Kintopf et al. | 548/260 |

FOREIGN PATENT DOCUMENTS

| | | |
|---|---|---|
| 52-113973 | 9/1977 | Japan . |
| 52-113974 | 9/1977 | Japan . |
| 1494823 | 12/1977 | United Kingdom . |
| 1494824 | 12/1977 | United Kingdom . |
| 1494825 | 12/1977 | United Kingdom . |

*Primary Examiner*—Donald G. Daus
*Attorney, Agent, or Firm*—Luther A. R. Hall

[57] ABSTRACT

Hologenated 2-(2-hydroxyphenyl)-2H-benzotriazoles of the formula

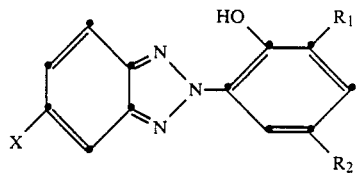

in which X is halogen, $R_1$ is hydrogen, $C_1$–$C_{12}$alkyl, $C_5$–$C_6$cycloalkyl, phenyl or phenyl-$C_1$–$C_4$alkyl and $R_2$ is $C_1$–$C_{12}$alkyl, $C_5$–$C_6$cycloalkyl, phenyl, phenyl-$C_1$–$C_4$alkyl or a group —$C_nH_{2n}$—COOR$_3$, in which n is 0 to 4 and $R_3$ is hydrogen or $C_1$–$C_{12}$alkyl, can be prepared particularly advantageously by catalytic hydrogenation of a corresponding o-nitroazo compound in the presence of a hydrogenation catalyst consisting of 0.1 to 3% of Pt on a support and of an organic amine.

18 Claims, No Drawings

PROCESS FOR THE PREPARATION OF BENZOTRIAZOLE DERIVATIVES

The present invention relates to a process for the preparation of halogen-containing 2-(2-hydroxyphenyl)-2H-benzotriazoles by catalytic hydrogenation of corresponding o-nitrophenylazohydroxyphenyl compounds in the presence of a Pt hydrogenation catalyst.

2-(2-Hydroxyphenyl)-2H-benzotriazoles are known from the literature as valuable UV absorbers. They are widely used in practice as light stabilizers for a large number of substrates, for example for stabilizing thermoplastics and coating materials (for example finishes), and also in various recording materials (for example in photographic layers and papers, and in printing inks and printing papers) and in textiles.

In line with the importance of these compounds, an extraordinarily large number of processes has already been proposed for preparing them. A major part of these starts from the abovementioned o-nitrophenylazo compounds and utilizes reductive cyclization in accordance with various reduction processes. One of these reduction processes is catalytic hydrogenation which has been described for the said benzotriazoles in a number of publications. If, however, halogen-containing o-nitrophenylazo compounds are hydrogenated, problems arise due to elimination of halogen. In order to overcome these, only certain hydrogenation catalysts could be used or additional measures had to be taken.

U.S. Pat. No. 3,978,074 describes a hydrogenation process of the abovementioned type, which is carried out in an alkaline and preferably aqueous medium, the hydrogenation catalysts being the conventional rare metal catalysts and other metal catalysts. It is pointed out in particular that dehalogenation of halogen-containing starting products takes place if metals (i.e. for example, Pt) are used as the catalyst. As a remedy, it is suggested to use sulfide catalysts (for example PtS, NiS and the like), in order to avoid dehalogenation.

According to GB-A-1,494,825 and 1,494,824, the hydrogenation is likewise carried out in an alkaline, purely aqueous (GB-A-1,494,825) or aqueous/organic (GB-A-1,494,824) medium. The hydrogenation catalysts used are rare metals, but Pd cannot be used as catalyst in the case of chlorine-containing nitroazo compounds. For the preparation of chlorine-containing benzotriazoles, Rh, especially 5% Rh on carbon, is used as the catalyst in each of the two cited GB-A-, from which it can be concluded that not only Pd but also Pt were regarded as unsuitable for the preparation of halogen-containing products.

The hydrogenation process described in GB-A-1,494,823 is carried out in organic solvent with the use of organic amines as bases and the conventional rare metal catalysts, Pd as catalyst being excluded in the case of chlorine substitution. Here again, 5% of Rh on carbon is used in the case of chlorine-substituted starting products (see page 3, left-hand column, 2nd paragraph; Examples 7 and 8).

U.S. Pat. No. 4,219,480 teaches the use of a nickel catalyst as the hydrogenation catalyst. Example 8 also demonstrates the preparation of a chlorine-containing benzotriazole, albeit at a not very high yield.

JP-A 52-113,973 deals specifically with the preparation of chlorine-substituted 2-(2-hydroxyphenyl)-2H-benzotriazoles by catalytic hydrogenation. The catalyst used is, inter alia, also 5% of platinum on carbon. It is found, however, that the yields are relatively low (see Examples 6 and 7) when usual bases such as NaOH and organic amines (for example triethylamine) are used. Only the use of unusual bases such as $NaBH_4$ or of so-called "superbases", for example 1,5-diazobicyclo[5,4,0]-undec-5-ene leads to somewhat higher yields. The same process is described in JP-A 52-113,974 for benzotriazoles which are not chlorine-substituted.

Surprisingly, it has now been found that, even if Pt is used as the hydrogenation catalyst, halogenated (especially chlorinated) 2-(2-hydroxyphenyl)-2H-benzotriazoles can be obtained in high yields without dehalogenation, even if simple amines are used as bases. This is made possible by the use of a Pt catalyst on a support which contains Pt in a quantity of 0.1–3% by weight.

In the process according to the invention for the preparation of 2-(2-hydroxyphenyl)-2H-benzotriazoles of the formula

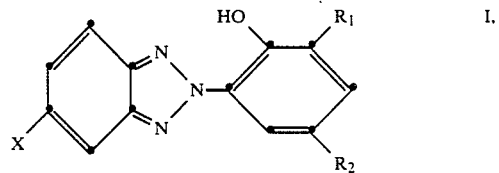

in which X is halogen, $R_1$ is hydrogen, $C_1$–$C_{12}$alkyl, $C_5$–$C_6$cycloalkyl, phenyl or phenyl-$C_1$–$C_4$alkyl and $R_2$ is $C_1$–$C_{12}$alkyl, $C_5$–$C_6$cycloalkyl, phenyl phenyl-$C_1$–$C_4$alkyl or a group —$C_nH_{2n}$—$COOR_3$, in which n is 0 to 4 and $R_3$ is hydrogen or $C_1$–$C_{12}$alkyl, by catalytic hydrogenation of an azo compound of the formula

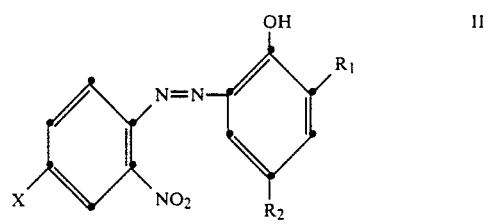

in the presence of a Pt hydrogenation catalyst and an organic amine, the hydrogenation catalyst used is Pt on a support, the Pt applied being 0.1 to 3% by weight.

In the formula I, halogen is chlorine, bromine or fluorine, especially chlorine. Phenyl-$C_1$–$C_4$alkyl ($R_1$, $R_2$) is especially benzyl, phenethyl, α-methylbenzyl and α,α-dimethylbenzyl, preferably benzyl. $R_3$ is preferably H or $C_1$–$C_4$alkyl, especially H or methyl. From the lower alkyl esters, in particular the methyl ester, compounds with $R_3$=H can be prepared by subsequent saponification, or compounds with other alkyl groups $R_3$ can be prepared by transesterification. The starting compounds of the formula II are known, for example from the printed publications quoted at the outset or from EP-A 57,160, or they can be prepared by the processes indicated therein, for instance by diazotization of an o-nitroaniline of the formula

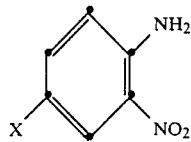

and coupling of the resulting diazonium salt with a phenol of the formula

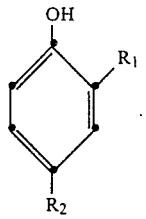

Preferably, compounds of the formula I are prepared in which X is chlorine, for example those compounds of formula I, in which $R_1$ is hydrogen, $C_1$–$C_{12}$alkyl or phenyl-$C_1$–$C_3$alkyl and $R_2$ is $C_1$–$C_{12}$alkyl, phenyl-$C_1$–$C_3$alkyl or a group —$C_2H_4COOR_3$, in which $R_3$ is H or $C_1$–$C_{12}$alkyl, especially H or $C_1$–$C_4$alkyl.

The preparation of compounds of the formula I, in which $R_1$ is hydrogen or $C_1$–$C_8$alkyl and $R_2$ is $C_1$–$C_8$alkyl, is of particular importance in practice.

It is essential to the invention that the Pt catalyst contains the Pt in an (applied) quantity of 0.1–3% by weight. It is advantageous to use catalysts in which Pt is present in a quantity from 0.2 to 2.5, especially 0.3–2, for example 0.5–1.5, and preferably 0.8–1.2% by weight.

The supports used can be those conventional in the technology of hydrogenation catalysts, for example carbon (for example activated carbon, wood charcoal, peat charcoal), Kieselguhr, alumina, barium sulfate and the like. The preferred support is carbon. Preferred catalysts according to the invention are therefore Pt/C catalysts, which contain the Pt in the quantities and preferred quantities indicated in the preceding paragraph.

The catalyst is advantageously employed in a quantity of 0.1–6%, especially 0.5–4%, for example 1.0–3.0%, relative to the o-nitroazo compound employed. The catalyst can of course be recycled, appropriately by filtration, as the process is carried out batchwise (discontinuously).

The organic amines used can be aliphatic, cycloaliphatic or aromatic amines. Examples of these are:

(1) Mono-, di- or tri-$C_1$–$C_{12}$alkylamines, especially $C_1$–$C_6$alkylamines and preferably $C_1$–$C_4$alkylamines (in which each alkyl chain can contain the indicated C number and the individual alkyl chains are identical or different), for example methylamine, ethylamine, n-propylamine, i-propylamine, n-butylamine, i-butylamine, t-butylamine, amylamine, dimethylamine, trimethylamine, diethylamine, triethylamine, di-n-propylamine, di-i-propylamine, tri-n-propylamine and di-n-butylamine.

(2) Mono- or poly-alkylenepolyamines. Examples of these are compounds of the formula $H_2N$—$C_nH_{2n}$(NH—$C_mH_{2m}$)$_p$—$NH_2$, in which p is a number from 0 to 4 and n and m independently of one another are a number from 1 to 6, the indices m being identical or different in the case of p>1. The alkylene chains are preferably unbranched radicals. In the case of polyalkylene polyamines (p≠0), the sum of all n+m is preferably 2–20, especially 4–18, for example 4–12. Particularly preferably, n and m independently of one another are a number from 2 to 4. The index p is preferably 0 (alkylenediamines) or a number from 1 to 3, especially 1 or 2 (polyalkylenepolyamines). The following are examples of amines from the class of monoalkylenepolyamines (alkylenediamines) and polyalkylenepolyamines: ethylenediamine, n-propylenediamine, n-butylenediamine, n-pentylenediamine, n-hexylenediamine, diethylenetriamine, triethylenetetramine, di-n- or i-propylenetriamine, tri-n- or i-propylenetetramine, di-n-butylenetriamine and tri-n-butylenetetramine.

(3) Mono-, di- and tri-$C_1$–$C_4$alkanolamines, for example monoethanolamine, diethanolamine, triethanolamine, mono-n-propanolamine, di-n-propanolamine and tri-n-propanolamine. (4) Cyclic amines having 5–7 C atoms, for example cyclohexylamine, methylcyclohexylamine and cyclopentylamine.

(5) Aromatic carbocyclic amines, in particular phenylamines, diphenylamines, $C_1$–$C_4$alkylphenylamines and phenyl-$C_1$–$C_3$alkylamines, for example aniline, o-, m- and p-toluidine, o-, m- and p-phenylenediamine, benzylamine, diphenylamine as well as N-$C_1$–$C_4$alkylanilines and N,N-di($C_1$–$C_4$alkyl)anilines such as N,N-dimethylaniline.

(6) Aromatic or aliphatic heterocyclic amines, in particular those having 5 or especially 6 ring members, for example pyridine, piperidine, piperazine, N-methylpiperazine and morpholine.

If heterocyclic amines are used, these are preferably monocyclic.

Preferred amines are those from the above groups (1), (2), (3) and (4), in particular (1), (2) and especially (1) and (2). Mono-, di- or tri($C_1$–$C_6$alkyl, especially $C_1$–$C_4$alkyl)amines or cyclohexylamine, especially methylamine, ethylamine, n-propylamine, i-propylamine, n-butylamine, i-butylamine, t-butylamine, cyclohexylamine, dimethylamine, diethylamine, di-i-propylamine, di-n-propylamine, di-n-butylamine, di-i-butylamine, trimethylamine or triethylamine are particularly preferably used in the process according to the invention, as are $C_2$–$C_6$alkylenediamines or polyalkylenepolyamines of the formula $H_2N$—$(CH_2)_{n'}$—$NH$—$(CH_2)_{m'}$—[NH—$(CH_2)_{p'}]_q$—$NH_2$ with n', m' and p'=2 to 4 (independently of one another) and q=0 or 1, in particular ethylenediamine, n-propylenediamine, n-butylenediamine, n-pentylenediamine, n-hexylenediamine, diethylenetriamine, triethylenetetramine, di-n-propylenetriamine, tri-n-propylenetetramine, di-n-butylenetriamine and tri-n-butylenetetramine, especially diethylenetriamine, triethylenetetramine, di-n-propylenetriamine, tri-n-propylenetetramine, ethylenediamine and n-propylenediamine.

As the base, mono-($C_1$–$C_4$alkyl)amines such as i-butylamine, n-butylamine, n-propylamine, i-propylamine, ethylamine and methylamine, especially the first two alkylamines mentioned and diethylamine, as well as $C_2$–$C_6$alkylenediamines or polyalkylenepolyamines such as ethylenediamine, n-propylenediamine, n-butylenediamine, diethylenetriamine and triethylenetetramine proved to be particularly advantageous.

The amine can also function as the reaction medium and sole solvent (especially when mono-, di- or tri-$C_1$–$C_6$alkylamines are used). In this case no further solvent for the reactants and the reaction product is required.

Advantageously, however, at least one further solvent is present in the reaction medium. This can be water or an organic solvent. If compounds of the formula I are prepared, where $R_2 = -C_nH_{2n}-COOR_3$ and $R_3 = H$, this additional solvent is preferably water, and in all other cases it is preferably an organic solvent. The latter can be solvents which are readily miscible with water (polar solvents) or are immiscible or sparingly miscible with water (non-polar solvents). If an organic solvent is also used in addition to the amine, the former is preferably a solvent which is immiscible or sparingly miscible with water, or a combination of the latter and a solvent readily miscible with water.

Examples of solvents which are immiscible or sparingly miscible with water (non-polar solvents) are hydrocarbons such as, say aliphatic hydrocarbons (for example hexane, heptane and petroleum ether); alicyclic hydrocarbons (for example cyclohexane and methylcyclohexane) as well as aromatic hydrocarbons (for example benzene, toluene, xylene) and also halogenated hydrocarbons, for example chlorobenzene, dichlorobenzene, trichlorobenzene, dichloroethane, dichloroethylene, trichloroethane and the like.

Examples of solvents which are readily miscible with water (polar solvents) are ethers, esters, ketones, amides (for example diethylether, dioxane, tetrahydrofuran, ethyl acetate, 1,2-dimethoxyethane, 1,2-di-ethoxyethane, acetone, ethyl methyl ketone, diethyl ketone, diisopropyl ketone, formamide, dimethylformamide and the like), trialkyl phosphates (for example triethyl phosphate) and especially alcohols, in particular lower aliphatic alcohols (having 1–6 and especially 1–4 C atoms) which are, for example, monohydric to trihydric, especially monohydric or dihydric and preferably monohydric. Examples of such alcohols are methanol, ethanol, n-propanol, isopropanol, sec-butanol, n-butanol, amyl alcohol, hexanol, ethylene glycol, diethylene glycol, 2-methoxyethanol.

The solvent used in the process according to the invention is particularly preferably an aromatic hydrocarbon, especially benzene, toluene or xylene, or a mixture of the said solvents with a lower aliphatic alcohol, in particular n-butanol or i- or n-propanol, and especially methanol or ethanol.

In the case of using water as the solvent used in addition to the amine, this can be used alone or in combination with water-miscible and/or water-immiscible organic solvents. Examples and preferences for such organic solvents are indicated above. A particularly preferred solvent system for the preparation of compounds of the formula I with $R_2 = C_nH_{2n}-COOR_3$ and $R_3 = H$ is the combination of water with a mono- or di-$C_1$-$C_4$alkylamine, in particular of water and diethylamine, preferably in a ratio of approximately 1:1.

If the organic amine does not function as the solvent, the amine is advantageously present in the reaction mixture in a quantity of at least 0.1 mol, especially at least 0.5 mol and preferably at least 0.9 mol to about 8 mol per mol of o-nitroazobenzole starting product. If the amine fulfills partially or wholly (as the sole solvent) the solvent function, it is employed in at least the quantity required for dissolving or dispersing the reaction components and products.

The process according to the invention can be carried out discontinuously (batchwise) or also continuously. For the continuous procedure, a fixed-bed catalyst, for example a high-pressure fixed-bed hydrogenation unit, is particularly suitable. In this case, the reaction mixture is taken off continuously, and fresh nitroazo compound plus amine (if appropriate plus solvent) is fed in.

In a particularly advantageous variant of the process according to the invention, which permits a continuous procedure and leads to high conversions and short reaction times, the catalyst in a part of the solvent is initially introduced into an autoclave, the autoclave is pressurized with hydrogen and the appropriate compound for the formula II, dissolved or dispersed in a further part of the solvent, is fed in, for example by means of a metering pump. The reaction solution can then be taken off continuously and the end product can be isolated from it in the usual manner. Alternatively, the catalyst can also be filtered off in a discontinuous procedure and the filtrate can be reprocessed appropriately.

The hydrogenation is advantageously carried out at temperatures of 0°–120° C., for example 15°–100° C. and especially 20°–80° C. Reaction temperatures of 25–50 and especially 30°–45° C. are particularly advantageous.

The hydrogen pressure during the hydrogenation can, for example, be in the range of 1–100, for example 1–50, especially 5–30 and preferably 10–20 bar. The hydrogen pressure applied depends mainly on the available hydrogenation unit. In high-pressure units, pressures of 100–200 bar are also possible. Such pressures are usual, especially in a continuous procedure.

The hydrogenation time can vary within wide limits and depends on the catalyst used, on the hydrogen pressure, on the reaction temperature and on the equipment used. It can be, for example, from 30 seconds to 5 hours, especially 10 minutes to 3 hours, for example 10 minutes to 2 hours. In a continuous procedure, for example, residence times from 1 to 60 minutes, especially from 1 to 30 minutes, are to be expected in practice.

The end products are isolated from the reaction medium by conventional methods known to those skilled in the art. It varies depending on the nature of the solvent used. An appropriate method comprises precipitation from the reaction mixture, which has been concentrated beforehand if necessary, by addition of a solvent in which the particular end product is sparingly soluble, and filtering off the precipitate. The working-up and any purification operations can also be taken from the examples.

As already mentioned at the outset, the 2-(2-hydroxyphenyl)-2H-benzotriazoles which can be prepared according to the invention are valuable UV absorbers which can be used in practice as light stabilizers for a large number of applications (as listed in the introduction, for example). Detailed possible uses of the said benzotriazoles are described in U.S. Pat. Nos. 3,055,896, 3,004,896, 3,072,585, 3,074,910, 3,189,615 and 3,230,194. The process according to the invention opens an idustrially particularly advantageous and economical route for the preparation thereof.

The examples which follow explain the process according to the invention in more detail. In the examples and in the remaining description and the patent claims, parts are parts by weight and percentage data are percent by weight, unless otherwise stated.

EXAMPLE 1

5-Chloro-2-(2-hydroxy-3-tert-butyl-5-methylphenyl)-2H-benzotriazole 60 g of 2-nitro-5-chloro-2'-hydroxy-3'-tert-butyl-5'-methylazobenzene (purity 86%), 40 g of xylene, 60 g of n-butylamine and 1 g of 1% Pt on activated carbon are put into a 300 ml hydrogenation reactor at room temperature under argon. Argon is then replaced by hydrogen. After the injection of 10 bar hydrogen, the hydrogenation is carried out at 35°-37° C. with intensive stirring. The heat released is removed by cooling. The end of the hydrogenation reaction is easily detectable by the hydrogen absorption ceasing after 2 mol equivalents of hydrogen, relative to the azobenzene starting product. The total hydrogenation time is about 1.5 hours.

After heating the reaction mass to 70°-80° C. the catalyst is separated off by filtration. The n-butylamine and a part of the xylene are removed from the filtrate by distillation. 150 g of methanol are then added to the resulting solution in xylene, and the desired product is thus precipitated. After cooling of the suspension to 0° C., the crystals (title compound) are filtered off and dried. Yield 43.3 g, corresponding to 91% of theory. Melting point 138°-140° C.

EXAMPLE 2

Example 1 is repeated, but with the difference that 100 g of n-butylamine are employed in place of 60 g of n-butylamine and 40 g of xylene. No influence on the hydrogenation rate or yield is observable. Neither is there an adverse effect of a replacement of xylene by toluene or benzene.

EXAMPLE 3

Examples 1 and 2 are repeated, but with the difference that the hydrogenation pressure is increased from 10 to 20 bar hydrogen. The hydrogenation time is shortened from about 1.5 hours to about 1 hour. The working-up is analogous, and virtually the same yield is obtained.

EXAMPLE 4

5-Chloro-2-(hydroxy-3,5-di-tert-butylphenyl)-2H-benztriazole

Examples 1 and 2 are repeated, but with the difference that an equivalent quantity of 2-nitro-5-chloro-2'-hydroxy-3',5'-di-tert-butylazobenzene (purity 91%) is employed in place of the 2-nitro-5-chloro-2'-hydroxy-3'-tert-butyl-5'-methylazobenzene. The title product is isolated in a yield of 46.1 g (92% of theory); melting point 154°-157° C.

EXAMPLE 5

When Example 4 in the variant according to Example 1 is repeated, but with the difference that n-butylamine is replaced by the equivalent quantity of diethylamine, the compound of Example 4 is obtained in a similar yield.

EXAMPLE 6

Example 4 in the variant according to Example 1 is repeated, but with the difference that the hydrogenation temperature is raised from 35°-37° C. to 60° C. As a result, the hydrogenation time is shortened from about 1.5 hours to about 0.5 hours. The product is isolated in a yield of 43.6 g (87% of theory).

EXAMPLE 7

Example 4 in the variant according to Example 1 is repeated, but with the difference that, in place of 1% Pt on activated carbon, the same quantity of 0.5% Pt on activated carbon is used as the catalyst. The product is then obtained in a yield of 93% of theory.

EXAMPLE 8

Example 4 in the variant according to Example 1 is repeated but with the difference that, in place of 1% Pt on activated carbon, the same quantity of 2% Pt on activated carbon is used as the catalyst. The product is then obtained in a yield of 86% of theory.

EXAMPLE 9

200 g of n-butylamine and 5.5 g of 1% Pt on activated carbon are introduced into a 2.1 hydrogenation reactor at room temperature under argon. The reactor is sealed and argon is replaced by hydrogen. After injection of 10 bar hydrogen, the catalyst is dispersed in the n-butylamine by intense stirring. At the same time, 300 g of 2-nitro-5-chloro-2'-hydroxy-3',5'-di-tert-butylazobenzene (purity 91%) are dispersed in 300 g of xylene at room temperature in an external vessel. This dispersion is pumped by means of an automatic metering device over a period of 1 hour against the hydrogen pressure into the hydrogenation reactor. The hydrogenation of the azo compound to the corresponding benzotriazole thus takes place at 20°-40° C.

After the end of the metered addition, the reaction mass is heated to 70°-80° C. and the catalyst is separated off by filtration. The further work-up is carried out analogously to Example 1 with correspondingly increased quantities of solvent. This gives 228 g (91% of theory) of 5-chloro-2-(2-hydroxy-3,5-di-tert-butylphenyl)-2H-benzotriazole of melting point 154°-157° C.

An increase in hydrogen temperature from 20°-40° C. to 50° C. or an increase in hydrogenation pressure from 10 to 20 bar or a shortening (lengthening) of the time of metered addition of the azo compound from 1 hour to 5 minutes (2 hours) has no significant effect on the product yield. Virtually the same yield is obtained.

EXAMPLE 10

5-Chloro-2-[2-hydroxy-3-tert-butyl-5-(2-methoxycarbonylethyl)-phenyl]-2H-benzotriazole 93 g of 2-nitro-5-chloro-2'-hydroxy-3'-tert-butyl-5'-carboxyethylazobenzene (purity 88%), 108 g of water, 108 g of diethylamine and 1.9 g of 1% Pt on activated carbon are introduced into a 1 l hydrogenation reactor at room temperature under argon.

Argon is then replaced by hydrogen. After the injection of 10 bar hydrogen, the hydrogenation is carried out at 40° C. with intensive stirring. The total hydrogenation time is about 1 hour. The end of the hydrogenation reaction is marked by the hydrogen absorption ceasing.

After heating the reaction mass to 60° C., the catalyst is separated off by filtration. The diethylamine and a part of the water are removed from the filtrate by distillation. 500 g of xylene are then added and the benzotriazolecarboxylic acid is transferred into the organic phase by acidification with about 15 g of sulfuric acid (83%). After the aqueous lower phase has been separated off, the xylene phase is concentrated by distillation and the benzotriazolecarboxylic acid is esterified (at about 70° C.) by the addition of 280 g of methanol and 10 g of sulfuric acid (concentrated); the product (title compound) then precipitates. The crystals are separated off and dried. (Yield 71.2 g, corresponding to 91% of theory). Melting point: 125°-128° C.

The 5-chloro-2-[2-hydroxy-3-tert-butyl-5-(2-carboxyethyl)phenyl]-2H-benzotriazole formed by the hydrogenation can, if desired, also be isolated as such from the reaction mixture, for example by acidifying the reaction mixture after the end of the hydrogenation and filtering off the precipitated product.

EXAMPLE 11

5-Chloro-2-(2-hydroxy-3,5-di-tert-butylphenyl)-2H-benzotriazole

Example 4 in the variant according to Example 1 is repeated, a mixture of 40 g of diethylenetriamine and 60 g of xylene being used in place of 60 g of n-butylamine and 40 g of xylene. The total hydrogenation time is 2 hours.

After the catalyst has been filtered off, the reaction solution is 2-phase (black, amine-rich lower phase and an upper xylene phase containing the product). The amine-rich lower phase can advantageously be separated off for improved working-up and re-use of the diethylenetriamine or can be left in the system.

The diethylenetriamine can be removed virtually quantitatively from the reaction solution by the addition of 20 g of water to the reaction solution and subsequent phase separation of the aqueous lower amine phase at about 80°–90° C.

After the usual working-up corresponding to Example 1, the title compound is isolated in a yield of 95% of theory.

An increase in the hydrogenation pressure from 10 to 50 bar shows no further effect apart from a shortening of the hydrogenation time. Virtually the same yield is obtained.

The use of an equivalent quantity of ethylenediamine or triethylene tetramine in place of 40 g of diethylenetriamine does not show any significant effect either on the course of the hydrogenation or on the product yield obtained.

EXAMPLE 12

When Example 4 in the variant according to Example 1 is repeated, but with the difference that either 40 g of monoethanolamine and 60 g of xylene or 40 g of cyclohexylamine and 60 g of xylene are used in place of 60 g of n-butylamine and 40 g of xylene, the compound of Example 4 is obtained in a slightly lower yield than in Example 4.

EXAMPLE 13

Example 4 in the variant according to Example 1 is repeated, a mixture of 30 g of xylene with 10 g of methanol being used in place of 40 g of xylene. The compound of Example 4 is isolated in a yield of 87% of theory.

EXAMPLE 14

Example 1 is repeated, but with the difference that a mixture of 40 g of diethylenediamine and 60 g of xylene is used in place of 60 g of n-butylamine and 40 g of xylene. After working-up of the reaction mass as indicated in Example 1, the reaction product is crystallized from xylene/methanol. This gives the compound of Example 1 in a yield of 92% of theory.

What is claimed is:

1. A process for the preparation of a 2-(2-hydroxyphenyl)-2H-benzotriazole of the formula

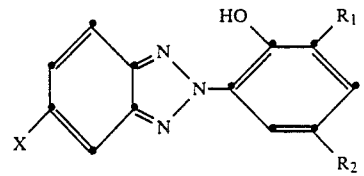

in which X is chloro, $R_1$ is hydrogen, $C_1$–$C_{14}$alkyl, $C_5$–$C_6$cycloalkyl, phenyl or phenyl-$C_1$–$C_4$alkyl and $R_2$ is $C_1$–$C_{12}$alkyl, $C_5$–$C_6$cycloalkyl, phenyl, phenyl-$C_1$–$C_4$alkyl group —$C_nH_{2n}$—COOR$_3$, in which n is 0 to 4 and $R_3$ is hydrogen or $C_1$–$C_{12}$alkyl, by catalytic hydrogenation of an azo compound of the formula

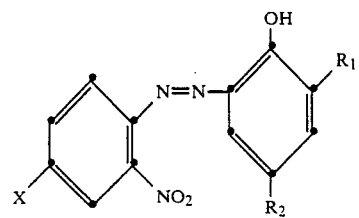

in the presence of a Pt hydrogenation catalyst and an organic amine, wherein the hydrogenation catalyst used is 0.1 to 3% Pt on a support.

2. A process according to claim 1, wherein $R_1$ is hydrogen, $C_1$–$C_{12}$alkyl or phenyl-$C_1$–$C_3$alkyl and $R_2$ is $C_1$–$C_{12}$alkyl, phenyl-$C_1$–$C_3$alkyl or a group —$C_2H_4$COOR$_3$, in which $R_3$ is hydrogen or $C_1$–$C_{12}$alkyl.

3. A process according to claim 2 wherein $R_3$ is hydrogen or $C_1$–$C_4$alkyl.

4. A process according to claim 3, wherein $R_1$ is hydrogen or $C_1$–$C_8$alkyl and $R_2$ is $C_1$–$C_8$alkyl.

5. A process according to claim 1, wherein 0.3 to 2% Pt on carbon is used as the catalyst.

6. A process according to claim 5, wherein 0.5–1.5% Pt on carbon is used as the catalyst.

7. A process according to claim 1, wherein the organic amine used is a mono-, di- or tri-$C_1$–$C_6$alkylamine, cyclohexylamine or a $C_2$–$C_6$alkylenediamine or a polyalkylenepolyamine of the formula $H_2N$—$(CH_2)_{n'}$—NH—$(CH_2)_{m'}$—[NH—$(CH_2)_{p'}$]$_q$—NH$_2$, in which n', m' and p' independently of one another are 2 to 4 and q is 0 or 1.

8. A process according to claim 7, wherein the amine is methylamine, ethylamine, n-propylamine, i-propylamine, n-butylamine, i-butylamine, t-butylamine, cyclohexylamine, dimethylamine, diethylamine, di-n-propylamine, di-i-propylamine, di-n-butylamine, trimethylamine, triethylamine, ethylenediamine, n-propylenediamine, n-butylenediamine, n-pentylenediamine, n-hexylenediamine, diethylenetriamine, triethylenetetramine, di-n-propylenetriamine, tri-n-propylenetetramine, di-n-butylenetriamine or tri-n-butylenetetramine.

9. A process according to claim 8, wherein the amine is diethylamine, i-butylamine, n-butylamine, ethylenediamine, n-propylenediamine, diethylenetriamine or triethylenetetramine.

10. A process according to claim 1, wherein the organic amine functions as the sole solvent.

11. A process according to claim 1, wherein an organic solvent which is immiscible or sparingly miscible with water is additionally added to the reaction mixture.

12. A process according to claim 11, wherein the organic solvent is a hydrocarbon.

13. A process according to claim 12, wherein the organic solvent is benzene, toluene or xylene.

14. A process according to claim 1, wherein, in the case of $R_2 = -C_nH_{2n}-COOR_3$ and $R_3 = H$, water is added additionally as a solvent.

15. A process according to claim 11, wherein a water-miscible organic solvent is added additionally to the reaction mixture.

16. A process according to claim 14, wherein a water-miscible organic solvent is added additionally to the reaction mixture.

17. A process according to claim 14, wherein a water-immiscible organic solvent is added additionally to the reaction mixture.

18. A process according to claim 15, wherein a water-immiscible organic solvent is added additionally to the reaction mixture.

* * * * *